United States Patent [19]
Barak et al.

[11] Patent Number: 5,891,646
[45] Date of Patent: Apr. 6, 1999

[54] METHODS OF ASSAYING RECEPTOR ACTIVITY AND CONSTRUCTS USEFUL IN SUCH METHODS

[75] Inventors: Lawrence S. Barak, Durham; Marc G. Caron, Hillsborough, both of N.C.; Stephen S. Ferguson, London, Canada; Jie Zhang, Durham, N.C.

[73] Assignee: Duke University, Durham, N.C.

[21] Appl. No.: 869,568

[22] Filed: Jun. 5, 1997

[51] Int. Cl.[6] .......................... G01N 33/52; C07H 21/04; C12N 15/12; C07K 14/00
[52] U.S. Cl. .......................... 435/7.2; 536/23.4; 530/350; 435/79.1; 435/69.1
[58] Field of Search .............................. 435/71, 174, 183, 435/6, 7.2, 69.1; 536/23.4, 23.5; 530/350

[56] References Cited

U.S. PATENT DOCUMENTS

| | | | |
|---|---|---|---|
| 5,284,746 | 2/1994 | Sledziewski et al. | 435/6 |
| 5,468,854 | 11/1995 | McCabe et al. | 540/498 |
| 5,482,835 | 1/1996 | King et al. | 435/6 |
| 5,491,084 | 2/1996 | Chalfie et al. | 435/189 |
| 5,532,157 | 7/1996 | Fink | 435/240.2 |
| 5,576,436 | 11/1996 | McCabe et al. | 546/156 |

FOREIGN PATENT DOCUMENTS

WO 98/12310 of 0000 WIPO.
WO94/16684 8/1994 WIPO.

OTHER PUBLICATIONS

L.S. Barak et al.; Internal Trafficking and Surface Mobility of a Functionally Intact $\beta_2$–Adrenergic Receptor–Green Fluorescent Protein Conjugate, *Mole. Pharm.* 51:177–184 (1997).

L. S. Barak et al.; The Conserved Seven–Transmembrane Sequence $(NP(X)_{2,3}Y)$ of the G–Protein–Coupled Receptor Superfamily Regulates Multiple Properties of the $\beta_2$–Adrenergic Receptor, *Biochem.* 34:15407–15414 (1995).

L. S. Barak et al., A Highly Conserved Tyrosine Residue in G Protein–coupled Receptors is Required for Agonist–mediated $\beta_2$–Adrenergic Receptor, *J. of Biological Chem.* 269, No. 4:2790–2795 (1994).

S. S. G. Ferguson et al.; Role of Phosphorylation in Agonist–promoted $\beta_2$–Adrenergic Receptor Sequestration, *The J. of Biological Chem.* 270, No. 42:24782–24789 (1995).

S. S. G. Ferguson et al.; Role of $\beta$–Arrestin in Mediating Agonist–Promoted G Protein–Coupled Receptor Internalization, *Science* 271:363–366 (1996).

S. S. G. Ferguson et al.; G–protein–coupled receptor regulation: role of G–protein–coupled receptor kinases and arrestins, *Can. J. Physiol. Pharmacol.* 74:1095–1110 (1996).

M. J. Lohse et al.; $\beta$–Arrestin: A Protein That Regulates $\beta$–Adrenergic Receptor Function, *Science* 248:1547–1550 (1990).

L. Ménard et al., Members of the G Protein–Coupled Receptor Kinase Family That Phosphorylate the $\beta_2$–Adrenergic Receptor Facilitate Sequestration, *Biochem.* 35:4155–4160 (1996).

M. Ormöl et al.; Crystal Structure of the Aequorea victoria Green Fluorescent Protein, *Science* 273:1392–1395 (1996).

Yokoe and Meyer, Spatial Dynamics of GFP–tagged proteins investigated by local fluorescence enhancement, *Nature Biotechnology* 14:1252 (Oct. 1996).

*Primary Examiner*—Lila Feisee
*Assistant Examiner*—Nirmal S. Basi
*Attorney, Agent, or Firm*—Myers Bigel Sibley & Sajovec

[57] ABSTRACT

Described are methods of detecting G-protein coupled receptor (GPCR) activity in vivo and in vitro; methods of assaying GPCR activity; and methods of screening for GPCR ligands, G protein-coupled receptor kinase (GRK) activity, and compounds that interact with components of the GPCR regulatory process. Constructs useful in such methods are described.

84 Claims, 9 Drawing Sheets

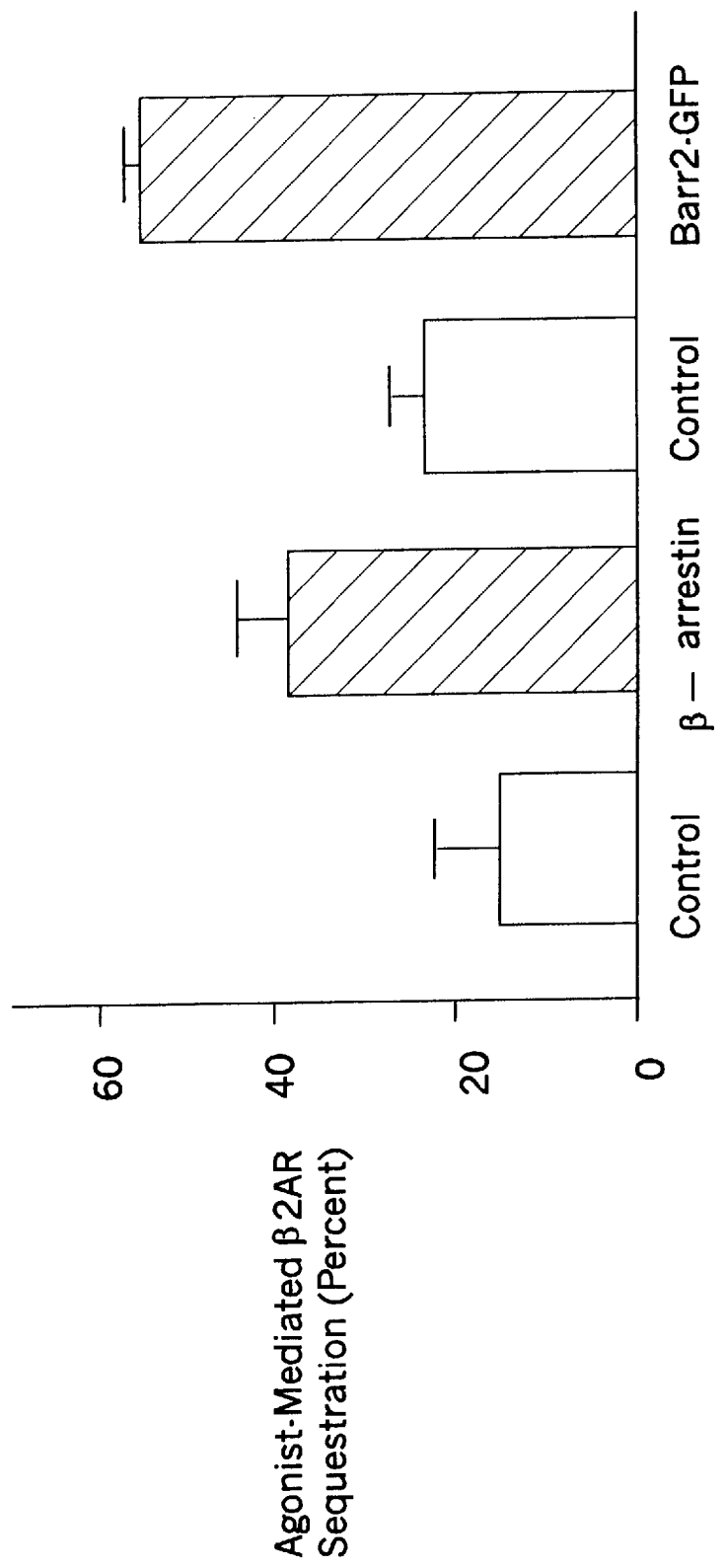

METHODS OF ASSAYING RECEPTOR ACTIVITY AND CONSTRUCTS USEFUL IN SUCH METHODS

FEDERALLY SPONSORED RESEARCH

This invention was made with Government support under National Institutes of Health Grant No. HL03422-02 and NS 19576. The Government has certain rights to this invention.

FIELD OF THE INVENTION

This invention relates to methods of detecting G-protein coupled receptor (GPCR) activity in vivo and in vitro, and provides methods of assaying GPCR activity, and methods of screening for GPCR ligands, G protein-coupled receptor kinase (GRK) activity, and compounds that interact with components of the GPCR regulatory process. This invention also provides constructs useful in such methods.

BACKGROUND OF THE INVENTION

The actions of many extracellular signals are mediated by the interaction of G-protein coupled receptors (GPCRs) and guanine nucleotide-binding regulatory proteins (G proteins). G protein-mediated signaling systems have been identified in many divergent organisms, such as mammals and yeast. GPCRs respond to, among other extracellular signals, neurotransmitters, hormones, odorants and light. GPCRs are similar and possess a number of highly conserved amino acids; the GPCRs are thought to represent a large 'super-family' of proteins. Individual GPCR types activate a particular signal transduction pathway; at least ten different signal transduction pathways are known to be activated via GPCRs. For example, the beta 2-adrenergic receptor (βAR) is a prototype mammalian GPCR. In response to agonist binding, βAR receptors activate a G protein ($G_s$) which in turn stimulates adenylate cyclase and cyclic adenosine monophosphate production in the cell.

It has been postulated that members of the GPCR superfamily desensitize via a common mechanism involving G protein-coupled receptor kinase (GRK) phosphorylation followed by arrestin binding. Gurevich et al., *J. Biol. Chem.* 270:720 (1995); Ferguson et al., *Can. J. Physiol. Pharmacol.* 74:1095 (1996). However, the localization and the source of the pool of arrestin molecules targeted to receptors in response to agonist activation was unknown. Moreover, except for a limited number of receptors, a common role for β-arrestin in GPCR desensitization had not been established. The role of β-arrestins in GPCR signal transduction was postulated primarily due to the biochemical observations.

Many available therapeutic drugs in use today target GPCRS, as they mediate vital physiological responses, including vasodilation, heart rate, bronchodilation, endocrine secretion, and gut peristalsis. See, eg., Lefkowitz et al., *Ann. Rev. Biochem.* 52:159 (1983). GPCRs include the adrenergic receptors (alpha and beta); ligands to beta ARs are used in the treatment of anaphylaxis, shock, hypertension, hypotension, asthma and other conditions. Additionally, spontaneous activation of GPCRs occurs, where a GPCR cellular response is generated in the absence of a ligand. Increased spontaneous activity can be decreased by antagonists of the GPCR (a process known as inverse agonism); such methods are therapeutically important where diseases cause an increase in spontaneous GPCR activity.

Efforts such as the Human Genome Project are identifying new GPCRs ('orphan' receptors) whose physiological roles and ligands are unknown. It is estimated that several thousand GPCRs exist in the human genome. With only about 10% of the human genome sequenced, 250 GPCRs have been identified; fewer than 150 have been associated with ligands.

SUMMARY OF THE INVENTION

A first aspect of the present invention is a conjugate of a β-arrestin protein and a detectable molecule. The detectable molecule may be an optically detectable molecule, such as Green Fluorescent Protein.

A further aspect of the present invention is a nucleic acid construct comprising an expression cassette. The construct includes, in the 5' to 3' direction, a promoter and a nucleic acid segment operatively associated with the promoter, and the nucleic acid segment encodes a β-arrestin protein and detectable molecule. The detectable molecule may be an optically detectable molecule such as Green Fluorescent Protein.

A further aspect of the present invention is a host cell containing a nucleic acid molecule which includes, a promoter operable in the host cell and a nucleic acid sequence encoding a β-arrestin protein and a detectable molecule. The detectable molecule may be an optically detectable molecule such as Green Fluorescent Protein. The cell may be a mammalian, bacterial, yeast, fungal, plant or animal cell, and may be deposited on a substrate.

A further aspect of the present invention is a method of assessing G protein coupled receptor (GPCR) pathway activity under test conditions, by providing a test cell that expresses a GPCR and that contains a conjugate of a β-arrestin protein and a visually detectable molecule; exposing the test cell to a known GPCR agonist under test conditions; and then detecting translocation of the detectable molecule from the cytosol of the test cell to the membrane edge of the test cell. Translocation of the detectable molecule in the test cell indicates activation of the GPCR pathway. Exemplary test conditions include the presence in the test cell of a test kinase and/or a test G-protein, or exposure of the test cell to a test ligand, or co-expression in the test cell of a second receptor.

A further aspect of the present invention is a method for screening a β-arrestin protein (or fragment of a β-arrestin protein) for the ability to bind to a phosphorylated GPCR. A cell is provided that expresses a GPCR and contains a conjugate of a test β-arrestin protein and a visually detectable molecule. The cell is exposed to a known GPCR agonist and then translocation of the detectable molecule from the cell cytosol to the cell edge is detected. Translocation of the detectable molecule indicates that the β-arrestin molecule can bind to phosphorylated GPCR in the test cell.

A further aspect of the present invention is a method to screen a test compound for G protein coupled receptor (GPCR) agonist activity. A test cell is provided that expresses a GPCR and contains a conjugate of a β-arrestin protein and a visually detectable molecule. The cell is exposed to a test compound, and translocation of the detectable molecule from the cell cytosol to the membrane edge is detected. Movement of the detectable molecule to the membrane edge after exposure of the cell to the test compound indicates GPCR agonist activity of the test compound. The test cell may express a known GPCR or a variety of known GPCRs, or express an unknown GPCR or a variety of unknown GPCRS. The GPCR may be, for example, an odorant GPCR or a β-adrenergic GPCR. The test cell may be a mammalian, bacterial, yeast, fungal, plant or animal cell.

A further aspect of the present invention is a method of screening a sample solution for the presence of an agonist to a G protein coupled receptor (GPCR). A test cell is provided that expresses a GPCR and contains a conjugate of a β-arrestin protein and a visually detectable molecule. The test cell is exposed to a sample solution, and translocation of the detectable molecule from the cell cytosol to the membrane edge is assessed. Movement of the detectable molecule to the membrane edge after exposure to the sample solution indicates the sample solution contains an agonist for a GPCR expressed in the cell.

A further aspect of the present invention is a method of screening a test compound for G protein coupled receptor (GPCR) antagonist activity. A cell is provided that expresses a GPCR and contains a conjugate of a β-arrestin protein and a visually detectable molecule. The cell is exposed to a test compound and to a GPCR agonist, and translocation of the detectable molecule from the cell cytosol to the membrane edge is detected. When exposure to the agonist occurs at the same time as or subsequent to exposure to the test compound, movement of the detectable molecule from the cytosol to the membrane edge after exposure to the test compound indicates that the test compound is not a GPCR antagonist.

A further aspect of the present invention is a method of screening a test compound for G protein coupled receptor (GPCR) antagonist activity. A test cell is provided that expresses a GPCR and contains a conjugate of a β-arrestin protein and a visually detectable molecule. The cell is exposed to a GPCR agonist so that translocation of the detectable molecule from the cytosol of the cell to the membrane edge of the cell occurs, and the cell is then exposed to a test compound. Where exposure to the agonist occurs prior to exposure to the test compound, movement of the detectable molecule from the membrane edge of the cell to the cytosol after exposure of the cell to the test compound indicates that the test compound has GPCR antagonist activity.

A further aspect of the present invention is a method of screening a cell for the presence of a G protein coupled receptor (GPCR). A test cell is provided that contains a conjugate of a β-arrestin protein and a visually detectable molecule. The test cell is exposed to a solution containing a GPCR agonist. Any translocation of the detectable molecule from the cytosol to the membrane edge is detected; movement of the detectable molecule from the cytosol to the membrane edge after exposure of the test cell to GPCR agonist indicates that the test cell contains a GPCR.

A further aspect of the present invention is a method of screening a plurality of cells for those cells which contain a G protein coupled receptor (GPCR). A plurality of test cells containing a conjugate of a β-arrestin protein and a visually detectable molecule are provided, and the test cells are exposed to a known GPCR agonist. Cells in which the detectable molecule is translocated from the cytosol to the membrane edge are identified or detected. Movement of the detectable molecule to the membrane edge after exposure to a GPCR agonist indicates that the cell contains a GPCR responsive to that GPCR agonist. The plurality of test cells may be contained in a tissue, an organ, or an intact animal.

A further aspect of the present invention is a substrate having deposited thereon a plurality of cells that express a GPCR and that contain a conjugate of a β-arrestin protein and a detectable molecule. Such substrates may be made of glass, plastic, ceramic, semiconductor, silica, fiber optic, diamond, biocompatible monomer, or biocompatible polymer materials.

A further aspect of the present invention is an apparatus for determining GPCR activity in a test cell. The apparatus includes means for measuring indicia of the intracellular distribution of a detectable molecule, and a computer program product that includes a computer readable storage medium having computer-readable program code means embodied in the medium. The computer-readable program code means includes computer-readable program code means for determining whether the indicia of the distribution of the detectable molecule in a test cell indicates concentration of the detectable molecule at the cell membrane, based on comparison to the measured indicia of the intracellular distribution of a detectable molecule in a control cell. The indicia of the intracellular distribution of the detectable molecule may be optical indicia, and the measuring means may be means for measuring fluorescent intensity. The molecule to be detected may be one that is fluorescently detectable, and the step of measuring the indicia of the intracellular distribution of the detectable molecule may include measurement of fluorescence signals from test and control cells.

A further aspect of the present invention is an apparatus for determining GPCR activity in a test cell. The apparatus includes means for measuring indicia of the intracellular distribution of a detectable molecule in at least one test cell at multiple time points, and a computer program product. The computer program product includes a computer readable storage medium having computer-readable program code means embodied in said medium. The computer-readable program code means includes computer-readable program code means for determining whether the indicia of the distribution of the detectable molecule in the test cell at multiple time points indicates translocation of the detectable molecule to the cell membrane.

A further aspect of the present invention is an apparatus for determining GPCR activity in a test cell, which includes means for measuring indicia of the intracellular distribution of a detectable molecule in at least one test cell, and a computer program product. The computer program product includes a computer readable storage medium having computer-readable program code means embodied therein and including computer-readable program code means for determining whether the indicia of the distribution of the detectable molecule in the test cell indicates concentration of the detectable molecule at the cell membrane, based on comparison to pre-established criteria.

BRIEF DESCRIPTION OF THE DRAWINGS

FIG. 2B shows the sequestration of β2AR in COS cells with and without overexpressed β-arrestin2 (left two bars) and with and without overexpressed βarr2-GFP (right two bars). Wild type β-arrestin2 and βarr2-GFP enhanced β2AR sequestration equally well above control levels, producing a 2.5 and 2.4 fold increase, respectively.

DETAILED DESCRIPTION OF THE INVENTION

Figure 1:
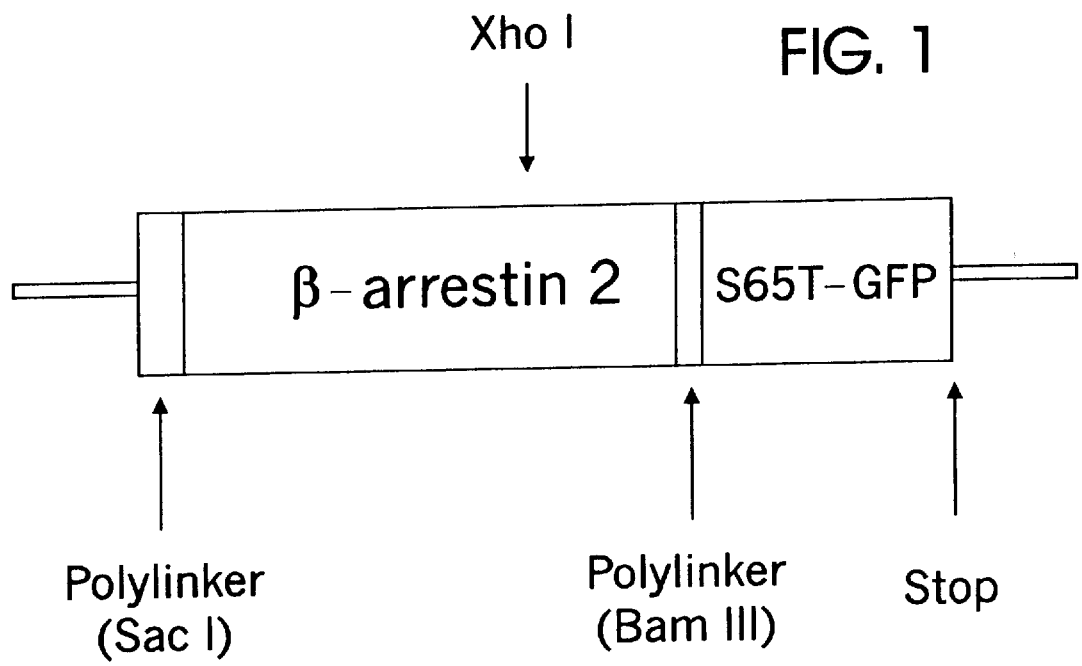
FIG. 1 is a linear model of the β-arrestin2/S65T-Green Fluorescent Protein (GFP) conjugate.

The present inventors have determined that β-arrestin redistribution from the cytosol to the plasma membrane occurs in response to agonist activation of GPCRs. The present inventors demonstrated a common role for β-arrestin in agonist-mediated signal transduction termination following agonist activation of receptors. The present inventors have devised convenient methods of assaying agonist stimulation of GPCRS in vivo and in vitro in real time. Although the pharmacology of members of the GPCR superfamily differs, the methods of the present invention utilize β-arrestin translocation to provide a single-step, real-time assessment of GPCR function for multiple, distinct members of the GPCR superfamily. The present methods may additionally be utilized in studying and understanding the mechanisms of actions of various therapeutic agents. The present inventors have determined that a protein conjugate or chimera comprising an arrestin molecule and a detectable molecule (such as Green Fluorescent Protein) is useful in such methods of assaying in vivo GPCR activity.

Due to the therapeutic importance of GPCRs, methods for the rapid screening of compounds for GPCR ligand activity are desirable. Additionally, methods of screening orphan GPCRs for interactions with known and putative GPCR ligands assist in characterizing such receptors. Optical methods are available for studying labelled protein dynamics in intact cells, including video microscopy, fluorescence recovery after photobleaching, and resonance energy transfer. However, such methods are of limited usefulness in labeling GPCRs for study, due to the relatively low level of GPCR expression and the alterations in receptor function that can occur after tagging or labeling of the receptor protein. Radiolabeling or fluorescent labeling of test ligands has also been utilized in screening for GPCR ligands. See, e.g. Atlas et al., *Proc. Natl. Acad. Sci. USA* 74:5490 (1977); U.S. Pat. No. 5,576,436 to McCabe et al. (all patents cited herein are incorporated herein in their entirety). The introduction of foreign epitopes into receptor cDNA to produce hybrid GPCRs is now a standard technique, and enhances detection of GPCRs by monoclonal antibody technology. However, such techniques are limited in their applicability to living cells. U.S. Pat. No. 5,284,746 to Sledziewski describes yeast-mammalian hybrid GPCRs and methods of screening for GPCR ligands using such hybrid receptors. U.S. Pat. No. 5,482,835 to King et al. describes methods of testing in yeast cells for ligands of mammalian GPCRs. However, application of these techniques to the study or identification of orphan GPCRs requires prior knowledge of ligands or signal transduction events and are therefor not generally applicable or universal.

Phosphorylation of GPCRs is a mechanism leading to desensitization of the receptors; receptors that have been continuously or repeatedly stimulated lose responsiveness, whereas the responses of other receptors remain intact. See Harden, *Pharmacol. Rev.* 35:5 (1983); Benovic et al., *Annu. Rev. Cell. Biol.* 4:405(1988). In a variety of cells, specific kinases have evolved for specific GPCRs. Desensitization occurs via the following pathway: agonist occupancy of the receptor transforms the receptor into an appropriate substrate for an associated kinase; β-arrestin binds to the kinase phosphorylated receptor and prevents subsequent interaction with the appropriate G-protein, as well as initiating both internalization and resensitization processes. Ferguson et al, *Science*, 271:363 (1996); Lohse et al., *Science* 248:1547 (1990). β-arrestin dependent desensitization is induced only when the GPCR is activated by ligand binding, and is an example of homologous desensitization (i.e., the ligand desensitizes only its target receptors). Lohse et al. (1990) and Attramadal et al., *J. Biol. Chem.* 267:17882 (1992) provide cDNA and amino acid sequences of β-arrestin. Various isoforms of β-arrestin are known; as used herein, β-arrestin refers to all such isoforms of β-arrestin, proteins having substantial sequence similarity thereto which are functional β-arrestins, and functional fragments thereof. Functional fragments of β-arrestin, its isoforms and analogs, may be determined using techniques as known in the art.

Molecules detectable by spectroscopic, photochemical, biochemical, immunochemical, electrical and optical means are known. Optically detectable molecules include fluorescent labels, such as commercially available fluorescein and Texas Red. Detectable molecules useful in the present invention include any biologically compatible molecule which may be conjugated to a β-arrestin protein without compromising the ability of β-arrestin to interact with the GPCR system, and without compromising the ability of the detectable molecule to be detected. Conjugated molecules (or conjugates) of β-arrestin and detectable molecules (which also may be termed 'detectably labelled β-arrestins') are thus useful in the present invention. Preferred are detectable molecules capable of being synthesized in the cell to be studied (e.g., where the cell can be transformed with heterologous DNA so that the βarrestin-detectable molecule chimera is produced within the cell). Particularly preferred are those detectable molecules which are inherently fluorescent in vivo. Suitable detectable molecules must be able to be detected with sufficient resolution within a cell that translocation of β-arrestin from the cytosol to the cell membrane in response to agonist binding to GPCR can be qualitatively or quantitatively assessed. Molecules detectable by optical means are presently preferred.

Fusion proteins with coding sequences for beta-galactosidase, firefly luciferase, and bacterial luciferase have been used in methods of detecting gene expression and protein interactions in cells. However, these methods require exogenously-added substrates or cofactors. In the methods of the present invention, an inherently fluorescent marker molecule is preferred, such as GFP, since detection of such a marker intracellularly requires only the radiation by the appropriate wavelength of light and is not substrate limited.

Green Fluorescent Protein (GFP) was first isolated from the jelly fish *Aequorea victoria*, and has an inherent green bioluminescence that can be excited optically by blue light or nonradiative energy transfer. Sequences of GFP-encoding cDNA and GFP proteins are known; see, e.g., Prasher et al., *Gene*, 111:229 (1992). The crystalline structure of GFP is described in Ormo et al., *Science* 273:1392 (1996). Purified native GFP absorbs blue light (maximally at 395 nm with a minor peak at 470 m) and emits green light (peak emission at 509 nm) (Morise et al, *Biochemistry*, 13:2656 (1974); Ward et al., *Photochem. Photobiol.*, 31:611 (1980)). It has been shown that GFP expressed in prokaryotic and eukaryotic cells produces a strong green fluorescence when excited by near UV or blue light (see U.S. Pat. No. 5,491,084 to Chalfie and Prasher); as this fluorescence requires no additional gene products from *A. victoria,* chromophore formation is not species specific and occurs either through the uses of ubiquitous cellular components or by autocatalysis. Expression of GFP in *Escherichia coli* results in an easily detected green fluorescence that is not seen in control bacteria. See Chalfie et al., *Science* 263:802 (1994); U.S. Pat. No. 5,491,084. Cells expressing the green-fluorescent proteins may be conveniently separated from those which do not express the protein by a fluorescence-activated cell sorter.

As used herein, Green Fluorescent Protein refers to the various naturally occurring forms of GFP which can be isolated from natural sources, as well as artificially modified GFPs which retain the fluorescent abilities of native GFP. As discussed in Ormo et al., *Science* 273:1392 (1996), various mutants of GFP have been created with altered excitation and emission maxima. Two characteristics of wild-type GFP which affect its usefulness in mammalian cell lines are the need to excite it at UV wavelengths to obtain a maximal fluorescent signal, and decreased fluorescence at temperatures over 23° C. However, the S65T/GFP mutant overcomes these limitations. Heim et al., *Proc. Natl. Acad. Sci. USA* 91:12501 (1994). Additional alterations in the GFP protein sequence which provide inherently fluorescent, biologically compatible molecules will be apparent to those in the art; sequence alterations may be made to alter the solubility characteristics of the protein, its excitation wavelength, or other characteristics, while retaining useful fluorescent properties. See, e.g. U.S. Pat. No. 5,625,048 to Tsien and Heim; WO 9711091 (Bjorn, Poulsen, Thastrup and Tullin); WO 9627675 (Haseloff, Hodge, Prasher and Siemering); WO 9627027 (Ward); WO 9623898 (Bjorn et al.); WO 9623810 (Heim and Tsien); WO 9521191 (Chalfie and Ward).

Cells useful in the methods of the present invention include eukaryotic and prokaryotic cells, including but not limited to bacterial cells, yeast cells, fungal cells, insect cells, nematode cells, plant or animal cells. Suitable animal cells include, but are not limited to HEK cells, HeLa cells, COS cells, and various primary mammalian cells. Cells contained in intact animals, including but not limited to nematodes, zebrafish (and other transparent or semi-transparent animals) and fruitflies, may also be used in the methods of the present invention. An animal model expressing a βarrestin-detectable molecule fusion protein throughout its tissues, or within a particular organ or tissue type, will be useful in studying cellular targets of known or unknown GPCR ligands.

Cells useful in the present methods include those which express a known GPCR or a variety of known GPCRs, or which express an unknown GPCR or a variety of unknown GPCRs. As used herein, a cell which expresses a GPCR is one which contains that GPCR as a functional receptor in its membrane; the cells may naturally express the GPCR(s) of interest, or may be genetically engineered to express the GPCR(s) of interest. As used herein, an 'unknown' or 'orphan' receptor is one whose function is unknown, and/or whose ligands are unknown.

The present experiments

Green fluorescent protein (GFP) has been used to study protein-protein interactions in living cells. See Kaether & Gerdes, *FEBS Lett.* 369:267 (1995); Olson et al., *J. Cell. Biol.* 130:639 (1995). Green fluorescent protein (GFP) is useful as a reporter molecule for fusion proteins due to its inherent fluorescence and its folding, which apparently isolates it from its conjugated partner. Prasher et al., *Gene* 111:229 (1992); Ormo et al., *Science* 273:1392 (1996). For example, a seven transmembrane protein as complex as the β2AR, which is three times larger than GFP, exhibits normal biochemistry after GFP conjugation to its C-terminus. Barak et al., *Mol. Pharmacol.* 51:177 (1997).

The present inventors established that a fusion protein consisting of a β-arrestin molecule (β-arrestin2) conjugated to a GFP at its C-terminus (βarr2-GFP, FIG. 1) is expressed in cells and is biologically active. The β-arr2-GFP fusion protein is approximately 50% larger than β-arrestin2, and this size increase is reflected by its slower migration on SDS-Page (FIG. 2A). The left lane of FIG. 2A, exposed to an antibody against β-arrestin, shows that βarr2-GFP runs more slowly than endogenous β-arrestin2 (highlighted middle band). The right lane of FIG. 2A, treated with a monoclonal anti-GFP antibody, demonstrates that the slower band does indeed contain GFP.

β2AR normally sequesters poorly in COS cells, and this has been correlated to the relatively poor expression of endogenous β-arrestins in COS cells. Menard et al., *Mol. Pharmacol.* 51:800 (1997); Zhang et al., *J. Biol. Chem.* 271:18302 (1996). Overexpression of exogenous β-arrestin enhances β2AR sequestration in these cells; similarly, as shown herein, βarr2-GFP overexpression in COS cells augmented β2AR internalization (FIG. 2B), demonstrating that βarr2-GFP is biologically active and equivalent to native β-arrestin.

Biochemical evidence indicates that β-arrestins are predominantly cytosolic proteins. Ferguson et al., *Can. J. Physiol. Pharmacol.* 74:1095 (1996). The present inventors, using confocal microscopy of βarr2-GFP in HEK-293 cells (FIG. 3A, left panel), confirmed that βarr2-GFP is distributed throughout the cytosol and excluded from the nucleus. The present data also establish for the first time that β-arrestin is not predominantly compartmentalized at the plasma membrane in the absence of agonist but that, upon addition of saturating concentrations of an agonist to the cell medium, β-arrestin is translocated from cell cytosol to cell membrane. Where β-arrestin is conjugated to an optically detectable molecule such as GFP, as shown herein, a rapid and readily observable optical enhancement of the membrane and a concomitant loss of cytosolic optical signals occurs (see FIGS. 3A and 3B, where membrane fluorescence is enhanced and cytosol fluorescence is decreased due to translocation of the βarrestin-GFP chimera).

To investigate whether the intracellular translocation of β-arrestin targeted binding sites in the plasma membrane other than the β2AR, the present inventors first crosslinked the receptors using monoclonal antibodies. As reported herein and shown in FIG. 4, the geometry of the agonist-induced time dependent translocation of β-arrestin to the plasma membrane mimicked the distribution of pre-aggregated β2ARs, indicating that the targeted site of β-arrestin is indeed β2AR or an associated component.

It has been postulated that phosphorylation of GPCRs by GRKs facilitates desensitization by increasing their affinity for β-arrestins. Gurevich et al, *J. Biol. Chem.* 268:16879 (1993); Gurevich et al., *J. Biol. Chem.* 268:11628 (1993). When expressed in HEK-293 cells and exposed to agonist, mutant Y326A-β2ARs are not significantly phosphorylated by endogenous GRKs (Ferguson et al., *J. Biol. Chem.*, 270:24782 (1995). Therefore, the present inventors utilized this mutant receptor to investigate the above question of β-arrestin affinity in vivo. Y326A-β2AR was cotransfected with βarr2-GFP into HEK cells in the absence and presence of co-transfected GRK. If the above hypothesis were true, reversal of phosphorylation impairment by overexpressed GRKs would result in a noticeable difference in βarr2-GFP translocation. As reported herein, without added GRK, βarr2-GFP translocation in response to agonist proceeded poorly; with the addition of GRK, βarr2-GFP translocation to the plasma membrane was much more robust (FIG. 5), indicating the importance of phosphorylation to β-arrestin activity.

The present inventors determined that translocation of β-arrestin from the cell cytosol to the cell membrane is an indicator of agonist stimulation of GPCR activity, and that a chimeric protein comprising β-arrestin and the detectable molecule GFP was capable of detectably displaying the real-time translocation of β-arrestin in response to agonist activation of GPCRs.

The results presented herein establish that β-arrestin targets GPCRs or an associated molecule following agonist binding and receptor phosphorylation. These data demonstrate a biological behavior for β-arrestin that has only been postulated from biochemical studies, and characterize for the first time how β-arrestin compartmentalization changes after initiation of receptor signal transduction. Agonist activation of a GPCR ultimately culminates in the association of β-arrestins with GPCRs, thus the visualization of the agonist mediated β-arrestin translocation process provides a universal indicator of GPCR activation.

The present inventors have demonstrated that GPCR signal transduction induces a rapid, substantial increase in the relative and absolute amount of plasma membrane bound β-arrestin. The agonist-mediated redistribution of β-arrestin coupled to a detectable molecule provides an optical amplification of the extracellular signals transduced by GPCRs, and this occurs simultaneous with, or within the same time frame as, the chemical amplification normally provided by second messenger cascades. Chimeras of β-arrestin and a detectable molecule are useful for the study of β-arrestin kinetics and GPCR related behavior such as endocytosis. Additionally, such chimeras are useful as biosensors for signaling when GPCRs become activated, and provide methods of screening compounds for GPCR activity, and screening orphan GPCRs for ligand responsiveness. In addition, the ability of co-transfected GRKs to enhance both the rate and extent of β-arrestin translocation indicate that the present methods and constructs can also be used to monitor GRK activity, as well as monitor drugs, proteins and compounds for activation or inhibition of the GRK/β-arrestin process.

The present invention provides a method for screening compounds for GPCR agonist activity, comprising: a) providing a cell expressing a known or unknown GPCR and containing a chimeric protein comprising a β-arrestin protein and a visually detectable protein; b) exposing the cell to a test compound; and c) detecting translocation of the detectable molecule from the cytosol of the cell to the membrane edge of the cell; where translocation of the detectable molecule from the cytosol to the membrane edge of the cell indicates activation of the GPCR and, accordingly, the GPCR activating effect of the test compound. Translocation of the chimeric protein is evidenced by an increase in the intensity of detectable signal located at the membrane edge (and/or a decrease in the cytosol), where the change occurs after exposure to the test compound. Translocation may thus be detected by comparing changes in the detectable signal in the same cell over time (i.e., pre and post test compound exposure). Alternatively, a test cell may be compared to a control cell (no exposure to test compound), or a test cell may be compared to a pre-established standard. If a known agonist is available the present methods can be used to screen for and study GPCR antagonists. Additionally, the membrane association of β-arrestin should be increased by expression of an excess of receptor or by a constitutively active GPCR that undergoes phosphorylation by GRKs even in the absence of agonist. Therefore, the present methods can be used to monitor for inverse agonists of GPCRs.

Methods of detecting the intracellular translocation of the chimeric protein will depend on the particular detectable protein utilized; one skilled in the art will be able to readily devise detection methods suitable for particular detectable molecules, given the teachings of the present specification and knowledge in the art. In a preferred embodiment, the visually detectable protein is a green-fluorescent protein (GFP) as discussed below.

The methods of the present invention provide easily detectable results. The translocation of β-arrestin coupled to a detectable molecule such as GFP, in response to GPCR activation, results in a relative enhancement of the detectable signal at the cell edge (i.e., at the cell membrane). In addition, the concomitant decrease in detectable signal from the cell cytosol means that 'background noise' (detectable signals which do not change in response to GPCR activation) is minimized. In certain cells, activation of GPCRs will result in essential clearing of detectable signal from the cytosol, and a 100-fold increase (or more) in the detectable signal at the cell membrane. In the present methods, it is preferred that the detectable signal at the membrane edge increase, after GPCR activation, at least two-fold, more preferably at least 3-fold, and more preferably at least 5-fold or at least ten-fold.

As used herein, the introduction of a chimeric protein into a cell may be accomplished by introducing into the cell (or the cell's ancestor) a nucleic acid (e.g., DNA or RNA) sequence or construct encoding the chimeric protein, and culturing the cell in an environment which allows expression of the chimeric protein. Introduction of nucleic acids encoding the chimeric protein, or introduction of the protein itself, into a cell may be carried out by any of the many suitable methods which are known in the art, including transfection, electroporation, microinjection, and liposome delivery.

The present invention provides a DNA construct comprising a promoter, DNA encoding a β-arrestin protein operatively associated therewith, and DNA encoding a visually detectable marker protein operatively associated therewith. The promoter is operatively associated with the encoding DNA; DNA encoding β-arrestin may be 5' from DNA encoding the visually detectable marker, or vice versa. In a preferred embodiment, the DNA encoding a visually detectable marker encodes a green-fluorescent protein (GFP). Vectors comprising such DNA constructs are a further aspect of the present invention.

The present invention further provides conjugates (such as chimeric proteins or fusion proteins) which comprise a β-arrestin protein and a visually detectable protein. In a preferred embodiment, the visually detectable protein is a green-fluorescent protein (GFP).

The present invention further provides a cell comprising a DNA molecule, which DNA molecule comprises, in the 5' to 3' direction, a promoter, DNA encoding a β-arrestin protein operatively associated therewith, and DNA encoding a visually detectable marker protein operatively associated therewith. In a preferred embodiment, the DNA encoding a visually detectable marker encodes a green-fluorescent protein (GFP).

The cells of the present invention may be used to detect the presence of specific molecules in various kinds of samples such as, e.g., aqueous samples, biological samples (for example blood, urine or saliva), environmental samples, or industrial samples. In such uses, the cells contain a GPCR whose agonists are known. Activation of the GPCR and the concomitant translocation of the detectable signal from the cytosol to the membrane edge indicates the presence of the agonist for the GPCR. A cell used in such a method may contain only a single type of known GPCR, or a variety of known GPCRs. Such detection will be useful for medical and veterinary diagnostic purposes; industrial purposes; and screening for drugs or chemicals of abuse or biological toxins that affect GPCR-mediated signal transduction.

The cells of the present invention may be deposited on, affixed to, supported by, or immobilized on a substrate. The substrate may be of any suitable material which is not harmful or detrimental to the living cells deposited thereon, i.e., which is bio-compatible with the living material deposited thereon. The substrate may be rigid, semi-rigid or flexible; and may be opaque, transparent, or semi-transparent. The size, geometry and other physical characteristics of the substrate will be dictated by the intended use, as will be apparent to one skilled in the art. Suitable substrates include, but are not limited to, plastics, glass, ceramics, silica, biocompatible monomer and polymer compositions, semiconductor materials, fiber optic materials, polystyrene, membranes, sephadex, and bio-organic materials. Examples of biocompatible materials are provided in U.S. Pat. Nos. 5,578,079; 5,575,997 and 5,582,834 to Leung and Clark; and U.S. Pat. No. 5,522,896 to Prescott.

The present invention further provides methods for screening for the presence of a GPCR agonist in a solution which comprises: a) providing a cell expressing a known or unknown GPCR and containing a chimeric protein comprising a β-arrestin protein and a visually detectable protein; b) exposing the cell to a test solution; and c) detecting translocation of the detectable molecule from the cytosol of the cell to the membrane edge of the cell; where translocation of the detectable molecule from the cytosol to the membrane edge of the cell indicates activation of the GPCR and, accordingly, the GPCR agonist effect of the test solution. Translocation of the chimeric protein is evidenced as discussed above.

The present invention further provides methods for screening for the presence of a GPCR antagonist in a solution which comprises: a) providing a cell expressing a GPCR and containing a chimeric protein comprising a β-arrestin protein and a visually detectable protein; b) exposing the cell to a test compound; then c) exposing the cell to a known agonist to the GPCR expressed in the cell; and d) detecting translocation of the detectable molecule from the cytosol of the cell to the membrane edge of the cell. If the test compound contains an antagonist, translocation of the detectable molecule will be delayed for a period of time corresponding to duration of antagonist action on the receptor (which time period will vary depending on the antagonist and/or the receptor). Translocation of the detectable molecule from the cytosol to the membrane edge of the cell indicates activation of the GPCR by the agonist. Accordingly, when translocation does not occur or is delayed (compared to that which would occur in the absence of test compound), the test compound contains an antagonist to the GPCR. Absence or delay of translocation may be assessed by comparison to a control cell (not exposed to test compound) or to a predetermined standard. Translocation of the chimeric protein is evidenced as discussed above. Exposure to the test compound and the known agonist may occur at essentially the same time, or exposure to the agonist may occur subsequent to exposure to the test compound. As used herein, subsequent exposure refers to exposure within the time period during which a potential antagonist would be expected to be interacting with the GPCR (i.e., binding to or bound to the GPCR).

The present invention further provides methods for screening a cell for the presence of a GPCR, comprising: a) providing a test cell; b) introducing into the test cell a chimeric protein comprising a β-arrestin protein and a visually detectable protein; and then c) exposing the cell to a test solution containing a known agonist to a GPCR; and d) detecting translocation of the detectable molecule from the cytosol of the cell to the membrane edge of the cell; where translocation of the detectable molecule from the cytosol to the membrane edge of the cell indicates activation of a GPCR and, accordingly, that the test cell contains such a GPCR. Translocation of the chimeric protein is evidenced as discussed above.

The present invention further provides methods for screening a cell population for the presence of cells containing GPCRs, comprising: a) providing a population of test cells, said test cells containing chimeric proteins comprising a β-arrestin protein and a visually detectable protein; and then b) exposing the cell population to a test solution containing an agonist to a GPCR; and d) detecting those cells in which translocation of the detectable molecule from the cytosol of the cell to the membrane edge of the cell occurs; where translocation of the detectable molecule from the cytosol to the membrane edge of a cell indicates activation of a GPCR and, accordingly, that the cell in question contains a GPCR. Translocation of the chimeric protein is evidenced as discussed above. Populations of cells to be screened include a collection of individual cells, a tissue comprising a plurality of similar cells, an organ comprising a plurality of related cells, or an organism comprising a plurality of tissues and organs.

As used herein, 'exposing' a cell to a test compound or solution means bringing the cell exterior in contact with the test compound or solution. Where the test compound or solution is being screened for GPCR ligand activity, exposure is carried out under conditions that would permit binding of a GPCR ligand to a receptor expressed in that cell. As used herein, 'translocation' of β-arrestin refers to movement of the β-arrestin molecule from one area of the cell to another.

The present methods may further be used to assess or study the effects of any molecule in the GPCR pathway which exerts its effect upstream of β-arrestin binding (i.e., prior to β-arrestin binding to the phosphorylated GPCR). Thus the present invention provides methods for assessing GPCR pathway functions in general. As used herein, the GPCR pathway refers to the series of events which starts with agonist activation of a GPCR followed by desensitization of the receptor via G protein-coupled receptor kinase (GRK) phosphorylation and β-arrestin binding.

In a broad sense the present invention thus provides a method of screening test compounds and test conditions for the ability to affect (activate or inhibit, enhance or depress) a GPCR pathway, and provides methods of assessing GPCR pathway function in a cell in general. In the present methods, the extent of translocation of β-arrestin is indicated by the degree of detectable changes in the cell; the extent of β-arrestin translocation is an indicator of the extent of GPCR pathway completion. The relative extent of translocation under varied test conditions may be compared, or a test condition may be compared to a control condition or to a predetermined standard.

For example, the specificity and effects of various kinases (including those known to interact with GPCR pathways and those not previously known to interact with GPCRs) for a specific GPCR or a group of GPCRs may be assessed by providing a test kinase to a test cell expressing a GPCR and containing a detectable β-arrestin molecule, exposing the cell to a GPCR agonist, and assessing the translocation of detectable β-arrestin from the cell cytosol to the cell membrane (see Example 7 herein). Translocation of the β-arrestin to the cell membrane indicates that the test kinase, in response to agonist occupancy of the receptor, is able to bind to and phosphorylate the receptor, so that β-arrestin will then bind to the kinase phosphorylated receptor and prevent subsequent interaction with the appropriate G-protein. In similar ways, the function of altered, recombinant or mutant kinases may be assessed; compounds may be screened for the ability to activate or inhibit the GPCR pathway, G protein-coupled receptor kinases, or β-arrestin binding; and the function of G-proteins may be assessed. For example, the following test conditions may be assessed using methods as described herein: the effects of G-proteins (including natural, heterologous, or artificially altered G-proteins) within the test cell; exposure of the test cell to known or putative GPCR ligands; and co-expression of a second receptor in the test cell expressing a GPCR.

Still further, the present methods allow the screening of β-arrestins (naturally occurring, artificially introduced, or altered, mutant or recombinant) for the ability to bind to a phosphorylated GPCR. In such methods, the test β-arrestin is conjugated to a detectable molecule such as GFP, and is placed within a cell containing a GPCR. The cell is exposed to a known agonist of the GPCR, and translocation of the detectable molecule from the cytosol of the cell to the membrane edge of the cell is detected. The translocation of the detectable molecule indicates that the test β-arrestin protein is able to bind to the phosphorylated GPCR. As in other methods of the present invention, the translocation may be compared to a control cell containing a known β-arrestin, or to a predetermined standard.

G Protein Coupled Receptors

GPCRs suitable for use in the present methods are those in which agonist binding induces G protein-coupled receptor kinase (GRK) phosphorylation; translocation of arrestin from the cytosol of the cell to the cell membrane subsequently occurs. As it is believed that virtually all members of the GPCR superfamily desensitize via this common mechanism, examples of suitable types of GPCRs include but are not limited to beta and alpha adrenergic receptors; GPCRs binding neurotransmitters (such as dopamine); GPCRs binding hormones; the class of odorant receptors (taste, smell and chemotactic receptors as found in nasal mucosa and the tongue, and on sperm, egg, immune system cells and blood cells); the class of type II GPCRs including secretin, glucagon, and other digestive tract receptors; light-activated GPCRs (such as rhodopsin); and members of the type III family of GPCRs which include but are not limited to metabotopic glutamate receptors and $GABA_B$ receptors. In addition to naturally occurring GPCRs, GPCRs may be specifically engineered or created by random mutagenesis. Such non-naturally occurring GPCRs may also be utilized in and screened by the present methods. The present methods may be utilized with any membrane receptor protein in which agonist binding results in the translocation of β-arrestin. Such receptors include growth factors that signal through G proteins.

Automated Screening Methods

The methods of the present invention may be automated to provide convenient, real time, high volume methods of screening compounds for GPCR ligand activity, or screening for the presence of a GPCR ligand in a test sample. Automated methods are designed to detect the change in concentration of labelled β-arrestin at the cell membrane and/or in the cytosol after exposure to GPCR agonist. The alteration of β-arrestin distribution can be detected over time (i.e., comparing the same cell before and after exposure to a test sample), or by comparison to a control cell which is not exposed to the test sample, or by comparison to pre-established indicia. Both qualitative assessments (positive/negative) and quantitative assessments (comparative degree of translocation) may be provided by the present automated methods, as will be apparent to those skilled in the art.

It is thus a further object of the present invention to provide methods and apparatus for automated screening of GPCR activity, by detecting the translocation of detectably labeled β-arrestin from cell cytosol to cell membrane in response to agonist activation of GPCRs. The translocation may be indicated by an alteration in the distribution of a detectable signal within a cell over time, between a test cell and a control cell, or by comparison to previously established parameters. In particular, according to one embodiment of the present invention, a plurality of cells expressing GPCRs and containing chimeric proteins comprising a detectable molecule and a β-arrestin molecule are provided. Indicia of the distribution of the detectable molecules are then measured using conventional techniques. In various embodiments, (a) measurement of optical indicia occurs before and after the addition of a test sample to a cell, and the time point measurements are compared; (b) optical indicia are measured in a test cell exposed to a test sample and in a non-exposed control cell, and these measurements are compared; and (c) measurement of a test cell after addition of a test sample is compared to preestablished parameters. The optical indicia being measured may be fluorescence signals (e.g., fluorescence intensities) if the detectable molecule of the chimeric β-arrestin protein is a fluorescent indicator such as GFP. Other optical indicia that are suitable for real-time measurement may also be used, as will be apparent to those skilled in the art.

An embodiment of the present invention includes an apparatus for determining GPCR response to a test sample. This apparatus comprises means, such as a fluorescence measurement tool, for measuring indicia of the intracellular distribution of detectable β-arrestin proteins in at least one test cell, and optionally also in a control or calibration cell. Measurement points may be over time, or among test and control cells. A computer program product controls operation of the measuring means and performs numerical operations relating to the above-described steps. The preferred computer program product comprises a computer readable storage medium having computer-readable program code means embodied in the medium. Hardware suitable for use in such automated apparatus will be apparent to those of skill in the art, and may include computer controllers, automated sample handlers, fluoresence measurement tools, printers and optical displays. The measurement tool may contain one or more photodetectors for measuring the fluorescence signals from samples where fluorescently detectable molecules are utilized in the detectable β-arrestin construct. The measurement tool may also contain a computer-controlled stepper motor so that each control and/or test sample can be arranged as an array of samples and automatically and repeatedly positioned opposite a photodetector during the step of measuring fluorescence intensity.

The measurement tool is preferably operatively coupled to a general purpose or application specific computer controller. The controller preferably comprises a computer program product for controlling operation of the measurement tool and performing numerical operations relating to the above-described steps. The controller may accept set-up and other related data via a file, disk input or data bus. A display and printer may also be provided to visually display the operations performed by the controller. It will be understood by those having skill in the art that the functions performed by the controller may be realized in whole or in part as software modules running on a general purpose computer system. Alternatively, a dedicated stand-alone system with application specific integrated circuits for performing the above described functions and operations may be provided.

As provided above, the indicia of β-arrestin distribution may take the form of fluorescent signals, although those skilled in the art will appreciate that other indicia are known and may be used in the practice of the present invention, such as may be provided by labels that produce signals detectable by fluorescence, radioactivity, colorimetry, X-ray diffraction or absorption or magnetism. Such labels include, for example, fluorophores, chromophores, radioactive isotopes (e.g., $^{32}P$ or $^{125}I$) and electron-dense reagents.

Definitions

As used herein, exogenous or heterologous DNA (or RNA) refers to DNA (or RNA) which has been introduced into a cell (or the cell's ancestor) through the efforts of humans. Such heterologous DNA may be a copy of a sequence which is naturally found in the cell being transformed, or a sequence which is not naturally found in the cell being transformed, or fragments thereof As used herein, the term 'gene' refers to a DNA sequence that incorporates (1) upstream (5') regulatory signals including a promoter, (2) a coding region specifying the product, protein or RNA of the gene, (3) downstream (3') regions including transcription termination and polyadenylation signals and (4) associated sequences required for efficient and specific expression.

Use of the phrase "substantial sequence similarity" in the present specification refers to DNA, RNA or amino acid sequences which have slight and non-consequential sequence variations from a sequence of interest, and are considered to be equivalent to the sequence of interest. In this regard, "slight and non-consequential sequence variations" mean that "similar" sequences (i.e., sequences that have substantial sequence similarity) will be functionally equivalent. Functionally equivalent sequences will function in substantially the same manner to produce substantially the same compositions.

As used herein, a "native DNA sequence" or "natural DNA sequence" means a DNA sequence which can be isolated from non-transgenic cells or tissue. Native DNA sequences are those which have not been artificially altered, such as by site-directed mutagenesis. Once native DNA sequences are identified, DNA molecules having native DNA sequences may be chemically synthesized or produced using recombinant DNA procedures as are known in the art.

As used herein, "a regulatory element" from a gene is the DNA sequence which is necessary for the expression of the gene, such as a promoter. In this invention, the term "operatively linked" to means that following such a link a regulatory element can direct the expression of a linked DNA sequence.

The term 'promoter' refers to a region of a DNA sequence that incorporates the necessary signals for the efficient expression of a coding sequence. This may include sequences to which an RNA polymerase binds but is not limited to such sequences and may include regions to which other regulatory proteins bind together with regions involved in the control of protein translation and may include coding sequences. Suitable promoters will be apparent to those skilled in the art, and will vary depending upon the cell in which the DNA is to be expressed. A suitable promoter for use in DNA constructs encoding a β-arrestin/detectable molecule construct may be a promoter naturally found in the cell in which expression is desired; optionally, the promoter of the β-arrestin within the construct may be utilized. Both inducible and constitutive promoters are contemplated for use in the present invention.

DNA Constructs

DNA constructs, or "expression cassettes," of the present invention include, 5' to 3' in the direction of transcription, a promoter, a DNA sequence operatively associated with the promoter, and, optionally, a termination sequence including stop signal for RNA polymerase and a polyadenylation signal for polyadenylase. All of these regulatory regions should be capable of operating in the cell to be transformed. Suitable termination signals for a given DNA construct will be apparent to those of skill in the art.

The term "operatively associated," as used herein, refers to DNA sequences on a single DNA molecule which are associated so that the function of one is affected by the other. Thus, a promoter is operatively associated with a DNA when it is capable of affecting the transcription of that DNA (i.e., the DNA is under the transcriptional control of the promoter). The promoter is said to be "upstream" from the DNA, which is in turn said to be "downstream" from the promoter.

The expression or transcription cassette may be provided in a DNA construct which also has at least one replication system. For convenience, it is common to have a replication system functional in *Escherichia coli,* such as Co1E1, pSC101, pACYC184, or the like. In this manner, at each stage after each manipulation, the resulting construct may be cloned, sequenced, and the correctness of the manipulation determined. In addition, or in place of the *E. coli* replication system, a broad host range replication system may be employed, such as the replication systems of the P-1 incompatibility plasmids, e.g., pRK290. In addition to the replication system, there will frequently be at least one marker present, which may be useful in one or more hosts, or different markers for individual hosts. That is, one marker may be employed for selection in a prokaryotic host, while another marker may be employed for selection in a eukaryotic host. The markers may be protection against a biocide, such as antibiotics, toxins, heavy metals, or the like; may provide complementation, by imparting prototrophy to an auxotrophic host; or may provide a visible phenotype through the production of a novel compound in the plant.

The various fragments comprising the various constructs, expression cassettes, markers, and the like may be introduced consecutively by restriction enzyme cleavage of an appropriate replication system, and insertion of the particular construct or fragment into the available site. After ligation and cloning the DNA construct may be isolated for further manipulation. All of these techniques are amply exemplified in the literature as exemplified by J. Sambrook et al., Molecular Cloning, A Laboratory Manual (2d Ed. 1989)(Cold Spring Harbor Laboratory).

The examples which follow are set forth to illustrate the present invention, and are not to be construed as limiting thereof. As used herein, βarr2-GFP=β-arrestin2 green fluorescent protein; GFP=green fluorescent protein; GPCR=G protein-coupled receptor; βARK=beta adrenergic receptor kinase; GRK=G protein-coupled receptor kinase; β2AR= beta 2 adrenergic receptor; HEK-293=human embryonic kidney cells; DMEM=Dulbecco's modified Eagle medium; and MEM=Minimal Essential Medium.

EXAMPLE 1

Materials and Methods

Materials: Isoproterenol was obtained from Sigma RBI. Anti-mouse antibody was obtained from Sigma Chemicals or Molecular Probes. Mouse monoclonal antibody against the 12CA5 epitope was obtained from Boehringer Mannheim. Cell culture media was obtained from Mediatech and fetal bovine serum from Atlanta Biologicals. Physiological buffers were from Gibco-Life Technologies Inc. Restriction enzymes were obtained from Promega or New England Biolabs, T4 ligase was from Promega, and Hot Tub DNA polymerase from Amersham. Commercially available plasmids containing variants of Green Fluorescent Protein were obtained from Clontech.

Cell Culture and Transfection: HEK-293 and COS cells were maintained and transfected as described by Barak et al., *Mol. Pharm.* 51:177 (1997). Cells containing both beta2 adrenergic receptor and β-arrestin constructs were transfected with between 5–10 µg of receptor cDNA in pcDNA1/ AMP and 0.5–1 µg of B arr2-GFP cDNA per 100 mm dish. GRKs were expressed using 5 µg of transfected cDNA in pcDNA1/AMP per dish.

Confocal Microscopy: HEK-293 cells transfected as described above were plated onto 35 mm dishes containing a centered, 1 cm well formed from a hole in the plastic sealed by a glass coverslip. Primary and secondary antibody labeling of live cells were performed at 37° C. for 30 minutes in media without serum in a 5% $CO_2$ incubator. Cells were washed three times between applications. Cells plated as above in MEM or DMEM buffered with 20 mM Hepes were viewed on a Zeiss laser scanning confocal microscope.

Sequestration: Flow cytometry analysis was performed using techniques known in the art, as described in Barak et al., *J. Biol. Chem.* 269:2790 (1994).

EXAMPLE 2

Construction of β-arrestin2-GFP Plasmid

β-arrestin2 cDNA in the plasmid pCMV5 was used as a template. Oligonucleotide primers surrounding a distal XhoI restriction site and the C-terminal stop codon of β-arrestin2 were used to replace the stop codon with an in frame BamHI restriction site by directed mutagenesis (Valette et al. *Nucleic Acids Res.* 17:723 (1989); Attramadal et al., *J. Biol. Chem.* 267:17882 (1992); Lohse et al., *Science* 248:1547 (1990)). The XhoI, BamHI segment was isolated. This segment was ligated to the N-terminal portion of β-arrestin cDNA (cut from pCMV5 by SacI and XhoI) in the polylinker of a plasmid that had been previously digested with SacI and BamHI and that contained S65T-Green Fluorescent Protein distal and in frame to the site of β-arrestin cDNA insertion. Lohse et al., *Science* 248:1547 (1990). The resulting β-arrestin-GFP construct was isolated following insertion and growth in *E. coli*. Constructs were verified by sequencing.

Figure 2A:
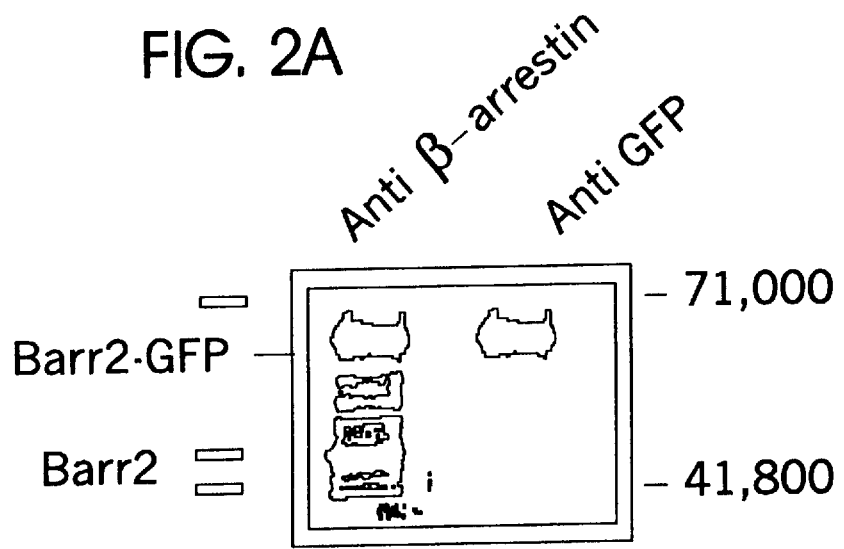
FIG. 2A provides the results of a Western Blot of homogenates of HEK-293 cells expressing the βarr2-GFP conjugate as well as endogenous β-arrestin2. βarr2 indicates endogenous cellular β-arrestin2; βarr2-GFP indicates βarrestin2-GFP conjugate; approximate molecular weights are indicated to the right of the gel. Land 1 was treated with anti-βarrestin antibody; Land 2 with anti-GFP antibody.

A linear model of the β-arrestin2/S65T-GFP conjugate is provided in FIG. 1.

EXAMPLE 3

Characterization of βarr2-GFP Expressed by HEK-293 Cells

Homogenates of HEK-293 cells transformed with the plasmid of Example 2 were studied using known Western Blot techniques. The results showed that HEK-293 cells expressed both endogenous β-arrestin and the βarr2-GFP conjugate.

Western Blots of homogenates of HEK-293 cells transfected with the plasmid of Example 2 and expressing βarr2-GFP were performed. An equal amount of homogenate material was loaded into each of two lanes (FIG. 2A). The left lane was exposed to anti-βarrestin antibody (Menard et al., *Mol. Pharm.* 51:800 (1997)), whereas the right lane was exposed to a mouse monoclonal antibody against GFP. The βarr2-GFP fusion protein is approximately 50% larger than β-arrestin2, and would thus be expected to migrate more slowly than β-arrestin on SDS-Page.

Exposure to anti-βarrestin antibody revealed multiple bars (left lane); exposure to anti-GFP monoclonal antibody revealed a single bar (right lane). The position of endogenous cellular β-arrestin2 is indicated by the intermediate bar in the left lane (βarr2). The heavy band just below 71,000 on the left lane (βarr2-GFP) is mirrored by a similar band in the right lane. In contrast, no band corresponding to endogenous cellular β-arrestin 2 is observed with anti-GFP antibody exposure. The treatment of the right lane with anti-GFP antibody demonstrated that the slower band labelled by anti-βarrestin antibody contained GFP.

EXAMPLE 4

Biological Activity of βarrestin-GFP Conjugate

β-arrestin activity can indirectly be assessed by measuring its effect on receptor sequestration (see Menard et al., *Mol.*

Pharm. 51:800 (1997); Ferguson et al., Science 271:363 (1996)). The β2AR normally sequesters poorly in COS cells, and this has been correlated to the relatively poor expression of endogenous β-arrestins (see Menard et al. Mol. Pharmacol. 51:800 (1997); Ferguson et al, Science 271:363 (1996)). Overexpression of exogenous β-arrestin enhances β2AR sequestration in these cells. To demonstrate that the βarr2-GFP conjugate is a biologically active β-arrestin, COS cells overexpressing βarr2-GFP were examined for augmentation of β2AR internalization, compared to the augmentation of βAR2 seen with the overexpression of β-arrestin2. Results are shown in FIG. 2B.

Using epitope tagged βAR2 receptors, sequestration of βAR2 was studied in COS cells overexpressing either (1) exogenous β-arrestin2 or (2) the βarr2-GFP conjugate. FIG. 2B shows the sequestration of β2AR in COS cells with and without overexpressed β-arrestin2 (left two bars) and with and without overexpressed βarr2-GFP (right two bars). Agonist mediated β2AR sequestration increased from 15±7% to 39±5% in the presence of overexpressed β-arrestin2; overexpression of βarr2-GFP similarly increased agonist mediated β2AR sequestration from 25±4% to 58±1%. Wild type β-arrestin2 and βarr2-GFP enhanced β2AR sequestration equally well above control levels, producing a 2.5 and 2.4 fold increase in β2AR sequestration, respectively.

The above results indicated that the βarr2-GFP conjugate acts as a biologically active arrestin.

EXAMPLE 5

Agonist Mediated Translocation of βarr2-GFP

Agonist mediated translocation of the βarr2-GFP chimera from cell cytosol to membrane was studied using HEK-293 and COS cells transfected with plasmids containing cDNA for the β2AR receptor and for the βarr2-GFP conjugate.

HEK-293 and COS cells were transfected with plasmids containing 10 µg of cDNA for β2AR and 0.5–1.0 µg for βarr2-GFP. Cells were assessed using confocal microscopy to detect the inherent intracellular fluorescence of GFP.

Figure 3A:
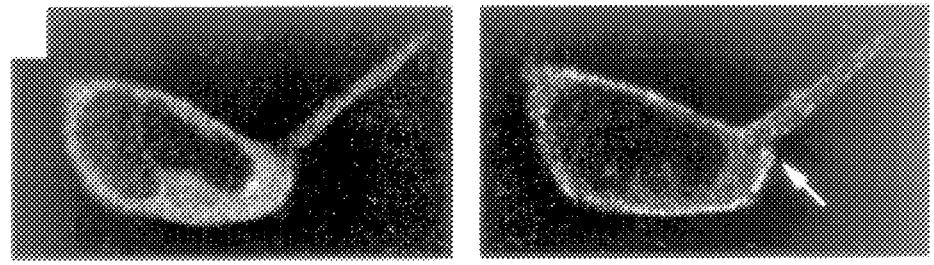
FIG. 3A: Confocal microscopy photomicrographs show βarr2-GFP translocation from cytosol (panel 1 at left) to membrane (panel 2 at right) in HEK-293 cells containing the β2AR, due to the addition of the βAR2 agonist isoproterenol. Bar=10 microns.

Transfected HEK-293 cells are shown in FIG. 3A, where panel 1 depicts cells prior to the addition of βAR2 agonist, and panel 2 depicts cells following the addition of agonist. Transfected COS cells are shown in FIG. 3B, where panel 1 depicts cells just prior to the addition of βAR2 agonist, and panel 2 depicts cells ten minutes after the addition of agonist.

As shown in FIG. 3A, βarr2-GFP distribution in HEK-239 cells was initially cytosolic (panel 1). No significant nuclear or membrane enhancement was apparent. Following the addition of the βAR2 agonist isoproterenol to the cell medium, the real-time agonist-mediated redistribution of βarr2-GFP was viewed using confocal microscopy. Ten minutes after isoproterenol addition (saturating concentrations), enhancement of membrane fluorescence was seen with a concomitant loss of cytosolic fluorescence, indicating that the βarr2-GFP distribution had shifted to the membrane (panel 2). These results establish that in HEK-293 cells containing the β2AR, βarr2-GFP expressed by the cell is translocated from cytosol to membrane following the addition of a βAR2 agonist. Exposure of the test cells to GPCR agonist enhanced membrane bound fluorescence tenfold over that seen prior to agonist exposure.

Figure 3B:
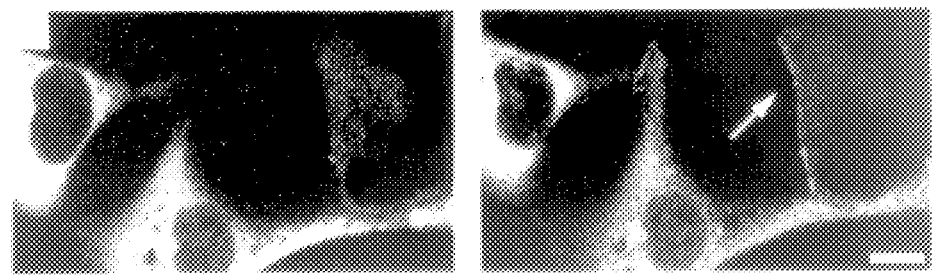
FIG. 3B: Confocal microscopy photomicrographs show βarr2-GFP translocation from cytosol (panel 1 at left) to membrane (panel 2 at right) in COS cells containing the β2AR, and due to addition of the βAR2 agonist isoproterenol. Bar=10 microns.

As shown in FIG. 3B, βarr2-GFP distribution in COS cells was initially cytosolic (panel 1). No significant nuclear or membrane enhancement was apparent. Following the addition of the βAR2 agonist isoproterenol to the cell medium, the real-time agonist-mediated redistribution of βarr2-GFP was viewed using confocal microscopy. Ten minutes after isoproterenol addition (saturating concentrations), enhancement of membrane fluorescence was seen with a concomitant loss of cytosolic fluorescence, indicating that the βarr2-GFP distribution had shifted to the membrane (panel 2). These results establish that in COS cells containing the β2AR, βarr2-GFP expressed by the cell is translocated from cytosol to membrane following the addition of a βAR2 agonist.

Comparing FIGS. 3A and 3B shows that the fluorescent signal is reduced in COS cells as compared to HEK cells, reflecting the lower efficiency of sequestration of the β2AR in COS cells. However, even in COS cells the shift of βarr2-GFP in COS cells from cytosol to membrane following the addition of βAR2 agonist is clearly discernible due to the fluorescence of the GFP moiety.

Figure 6A:
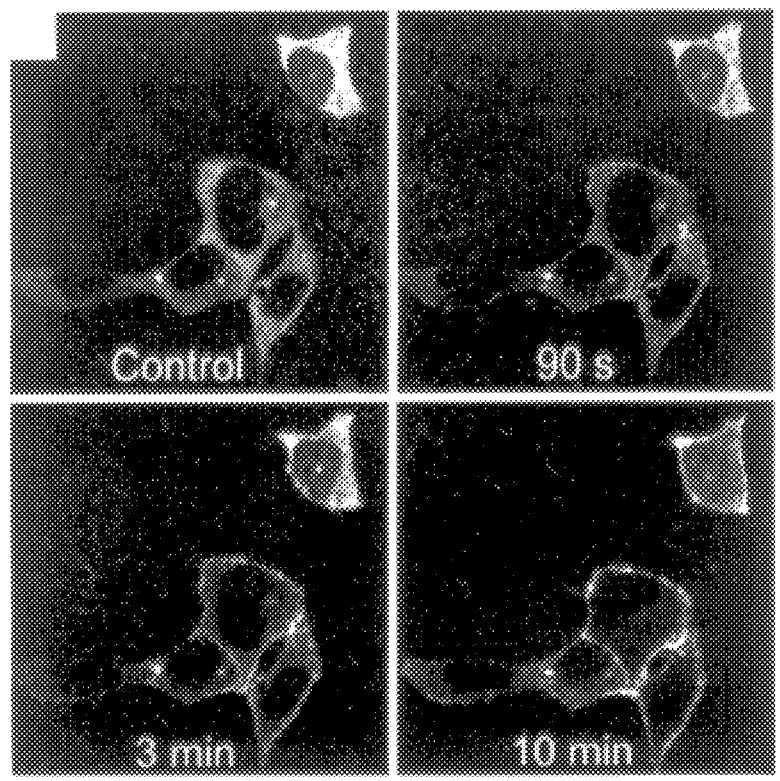
FIG. 6A depicts the agonist-induced time dependent translocation of βarr2-GFP to beta2 adrenergic receptors in a representational HEK-293 cell.
Figure 6B:
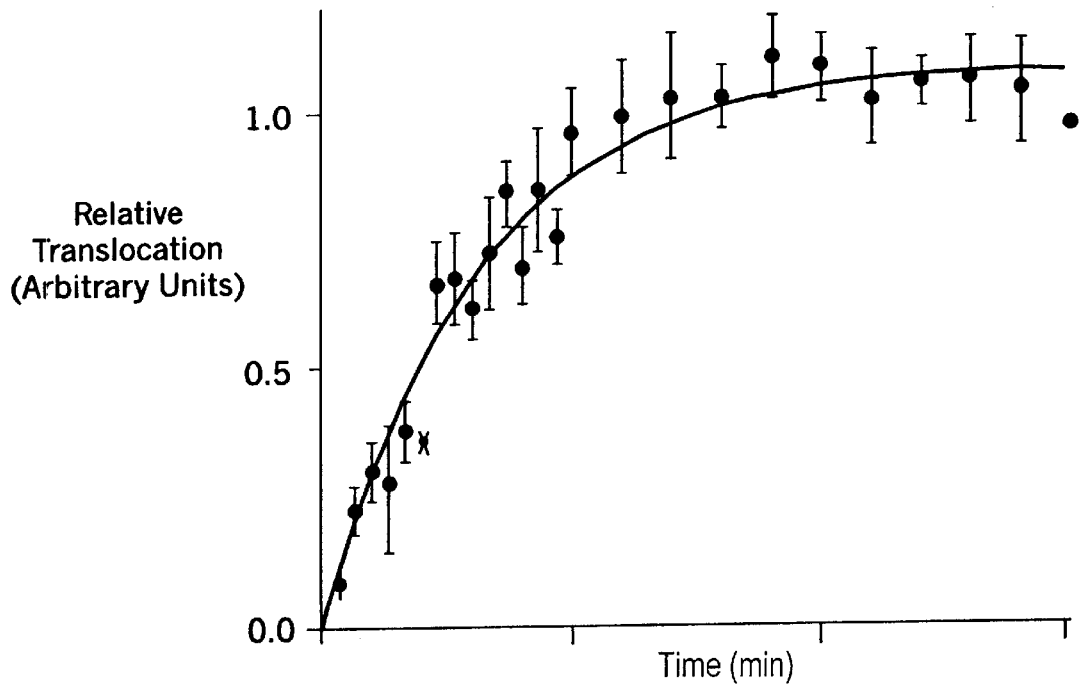
FIG. 6B graphs the time course of agonist-induced translocation of βarr2-GFP to beta2 adrenergic receptors in HEK-293 cells; this graph is quantitative and is based on the responses of a plurality of cells.
Figure 6D:
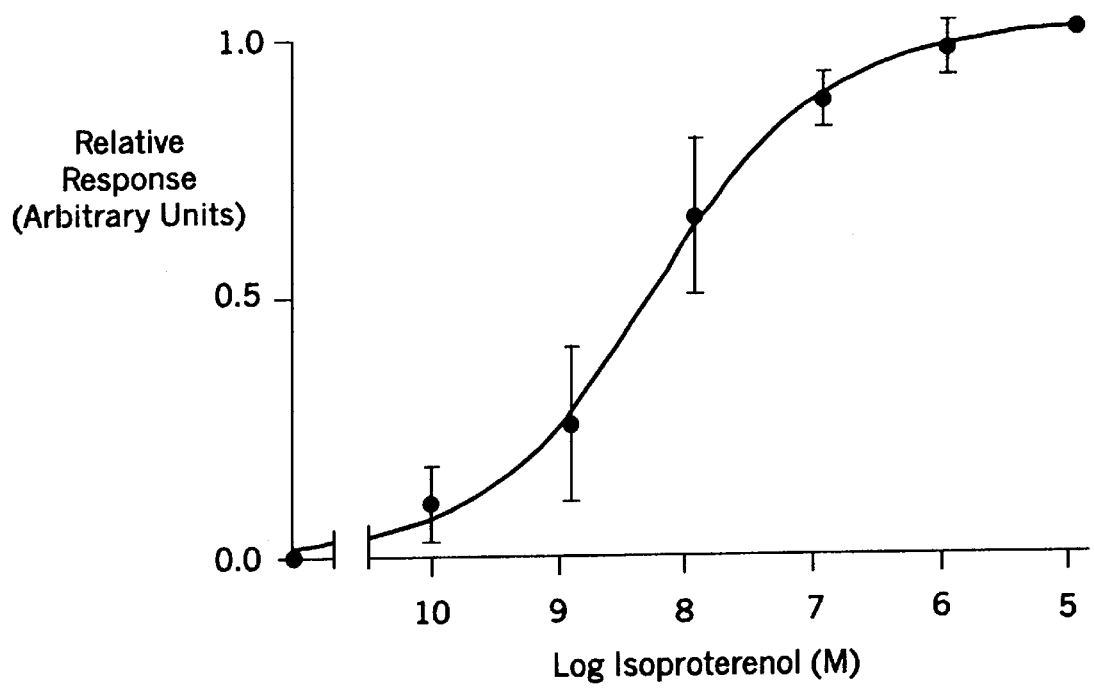
FIG. 6D graphs the dose dependent agonist-induced translocation of βarr2-GFP to beta2 adrenergic receptors in HEK-293 cells; this graph is quantitative and is based on the responses of a plurality of cells.
Figure 6C:
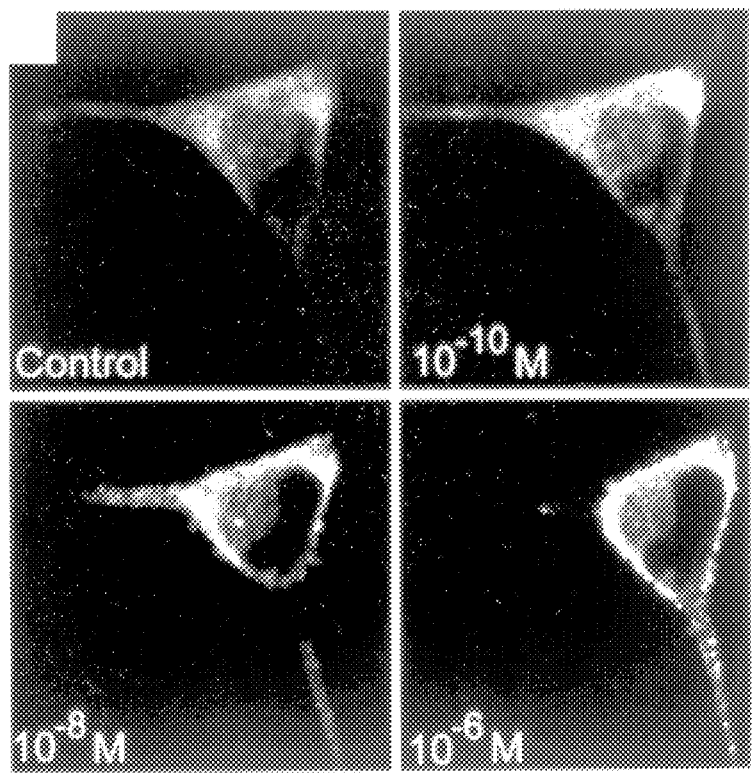
FIG. 6C is depicts the agonist-induced translocation of βarr2-GFP to beta2 adrenergic receptors in representational HEK-293 cells, at varying doses of agonist.
Figure 6E:
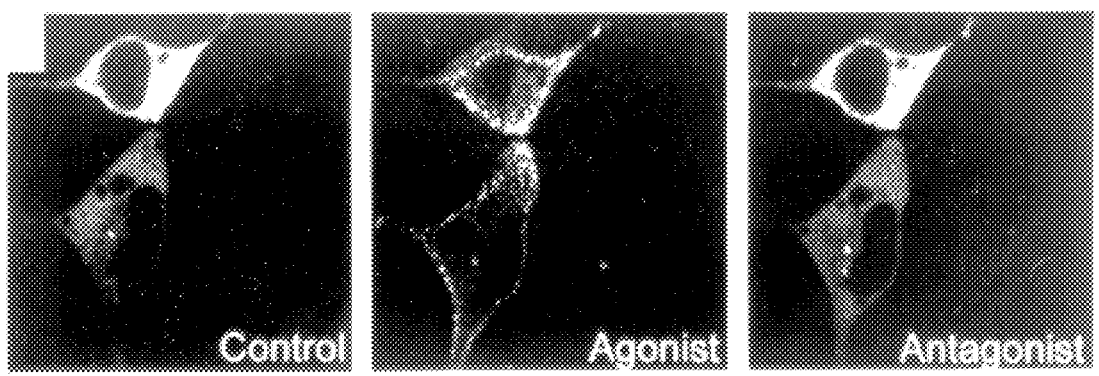
FIG. 6E evaluates the translocation of βarr2-GFP from the cell cytosol to the cell membrane, in response to exposure to receptor agonist (middle panel) and subsequent exposure to receptor antagonist (right panel).

The above experiments with COS and HEK-239 cells were reproduced except that the β2AR antagonist propranolol was added to the cell medium. Using confocal microscopy to visually track βarr2-GFP in the cell in real time, as above, indicated that no shift in βarr2-GFP from cytosol to membrane occurred in response to a βAR2 antagonist. As shown in FIG. 6E, addition of an agonist (middle panel) resulted in translocation of βarr2-GFP from cytosol to membrane; subsequent addition of an antagonist (right panel) reversed the translocation (compare to control, left panel).

Biochemical evidence indicates that β-arrestins are predominantly cytosolic proteins. Ferguson et al, Can. J. Physiol. Pharmacol. 74:1095 (1996). The present results confirm that βarr2-GFP is distributed throughout the cytosol and excluded from the nucleus. These data also establish that βarr2-GFP is not predominantly compartmentalized at the plasma membrane in the absence of agonist, but that upon exposure to an agonist the cellular βarr2-GFP shifts to the membrane. The present results further indicate that the shift of the βarr2-GFP conjugate in response to the addition of a G protein coupled receptor agonist can be detected optically as an enhancement of membrane fluorescence and/or a concomitant loss of cytosolic fluorescence, and that this response is rapidly observed.

EXAMPLE 6

Intracellular βarr2-GFP Targets Membrane Receptors

Figure 4A:
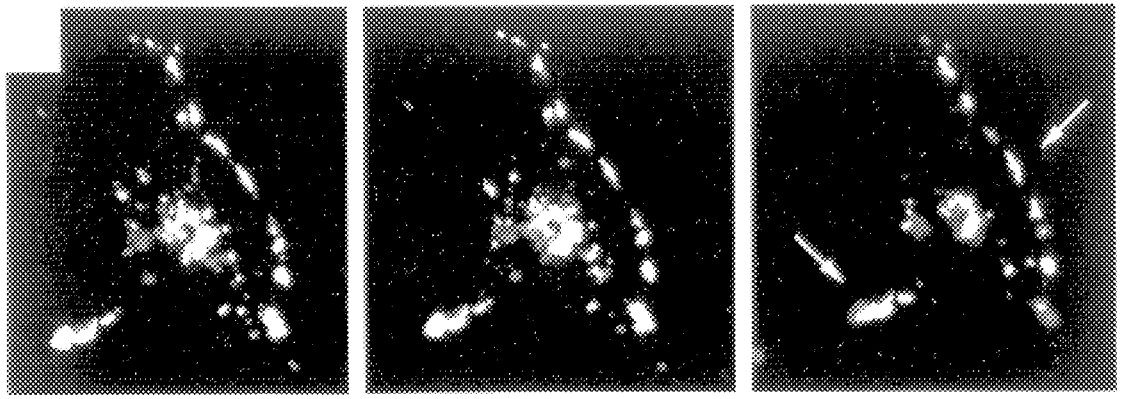
FIG. 4 depicts a HEK-293 cell containing 12CA5(HA) tagged β2AR (confocal microscopic photographs). Row A shows a cell after reorganization of β2AR into plasma membrane clusters. Row B provides three pictures of the same cell at 0, 3, and 10 minutes (left to right) after the addition of agonist. Redistribution of βarr2-GFP to the cell membrane is shown by the enhancement of membrane fluorescence with a concomitant loss of cytosolic fluorescence. Arrows indicate areas of co-localization; bar=10 microns.
Figure 4B:
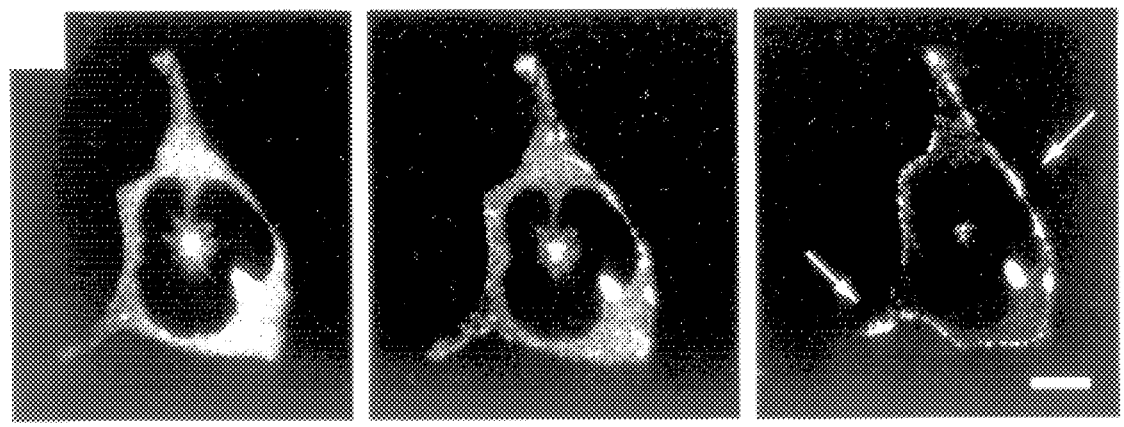

FIG. 4 shows the time course of βarr2-GFP redistribution to plasma membrane 12CA5(HA) tagged β2AR in HEK-293 cells, as shown by confocal microscopy.

The present example demonstrates that β2ARs are the target of intracellular βarr2-GFP conjugate proteins. HEK-239 cells containing 12CA5(HA) tagged β2AR receptors were studied. The receptors in the HEK-293 cells were reorganized into plasma membrane clusters (Row A) by crosslinking with a mouse monoclonal antibody directed against an N-terminal epitope, followed by Texas Red conjugated goat anti-mouse antibody. In FIG. 4, the three panels of Row A show the same HEK-293 cell with βAR2 receptors reorganized into plasma membrane clusters.

HEK-239 cells were then exposed to agonist (isoproterenol added to cell medium, as above); the three panels of Row B in FIG. 4 were taken consecutively after agonist addition (left to right, at 0, 3 and 10 minutes post agonist addition). The real-time redistribution of βarr2-GFP to the receptors over a ten minute time period is thus demonstrated by comparing the panels of Row A and Row B of FIG. 4. In FIG. 4, arrows indicate areas of colocalization and the bar=10 microns.

FIG. 4 demonstrates that the geometry of the agonist-induced time dependent translocation of βarr2-GFP to the plasma membrane mimicked the distribution of pre-aggregated β2ARs. This indicates that the primary site targeted by β-arrestin is the β2AR or a closely associated component.

EXAMPLE 7

Intracellular βarr2-GFP Targets Membrane Receptors

It has been postulated that phosphorylation of GPCRs by GRKs facilitates desensitization by increasing their affinity for β-arrestins. Gurevich et al., *J. Biol. Chem.* 268:16879 (1993); Gurevich et al, *J. Biol. Chem.* 268:11628–11638 (1993); Ferguson et al., *Can. J. Physiol. Pharmacol.* 74:1095 (1996). When expressed in HEK-293 cells and exposed to agonist, mutant Y326A-β2ARs are not significantly phosphorylated by endogenous GRKs. Barak et al., *Biochem.* 34:15407 (1995); Ferguson et al., *J. Biol. Chem.* 270:24782 (1995). This phosphorylation impairment in Y326A-βAR2s is reversed by overexpression of GRKs in the same cell. Menard et al., *Biochem.* 35:4155 (1996). The Y326A mutant receptor was used to investigate β-arrestin affinity in vivo; the effect of overexpressed GRK on the Y326A-B2AR interaction with βarr2-GFP was shown.

Y326A-β2AR and βarr2-GFP were co-transfected into HEK-239 cells, in the absence and presence of co-transfected GRK. If phosphorylation of GPCRs by GRKs facilitates desensitization by increasing their affinity for β-arrestins, then overexpression of GRK would result in a noticeable difference in βarr2-GFP translocation.

Figure 5A:
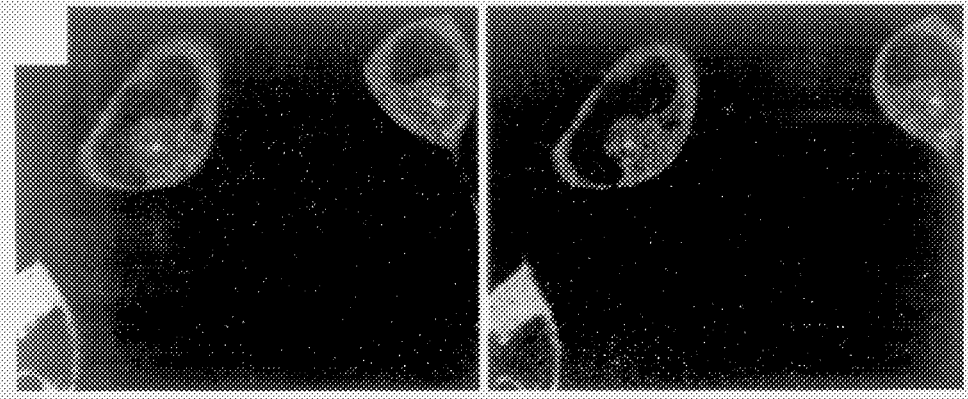
FIG. 5 shows the influence of overexpressed GRK on the redistribution of βarr2-GFP in HEK-293 cells expressing the Y326A phosphorylation-impaired β2AR. Cells without (Row A) and with (Row B) overexpressed GRKs were exposed to agonist, and the real-time redistribution of βarr2-GFP was observed. βarr2-GFP translocation in cells containing overexpressed GRK (Row B) was more robust, indicating an increased affinity of βarr2-GFP for receptor. Bar=10 microns.
Figure 5B:
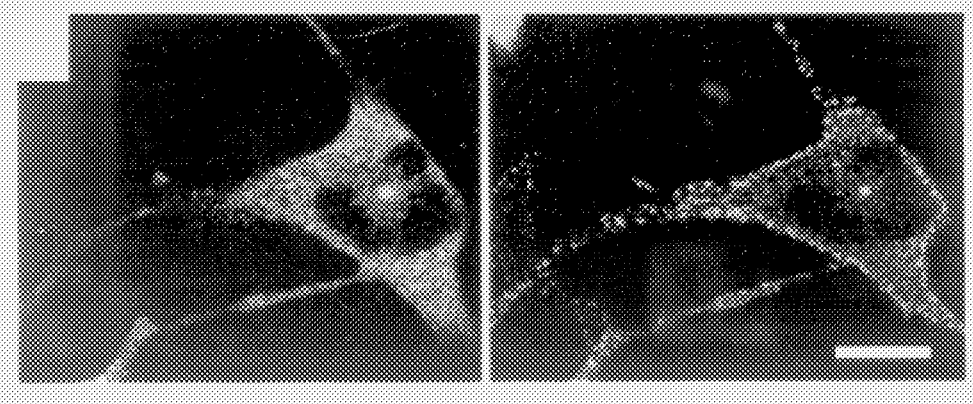

FIG. 5 shows the influence of overexpressed GRK on the redistribution of βarr2-GFP in HEK-293 cells expressing the Y326A phosphorylation impaired β2AR. Cells without (Row A) and with (Row B) overexpressed GRKs were exposed to agonist, and the real-time redistribution of βarr2-GFP was observed. Without added GRK, βarr2-GFP translocation in response to agonist proceeded poorly, as shown in Row A of FIG. 5. βarr2-GFP translocation in cells containing overexpressed GRK (Row B) was more robust, indicating an increased affinity of βarr2-GFP for receptor and the relationship of phosphorylation and β-arrestin activity.

EXAMPLE 8

Testing of Additional Receptors in the β2AR/rhodopsin Subfamily

Twelve different members of the β2AR/rhodopsin subfamily of GPCRs have been studied. Cells expressing a particular GPCR, and containing βarrestin-GFP chimeric proteins were exposed to known agonists for the GPCR being studied. In each case, an observable translocation of the βarrestin-GFP chimeric proteins from the cell cytosol to the cell membrane was produced within minutes following addition of the GPCR agonist (data not shown).

That which is claimed:

1. A method of assessing the effect of a test condition on G protein coupled receptor (GPCR) pathway activity, comprising:
    a) providing a cell that expresses a GPCR, and that contains a conjugate comprising a β-arrestin protein and an optically detectable molecule;
    b) exposing the cell to an agonist for said GPCR under said test condition;
    c) detecting translocation of the detectable molecule from the cytosol of the cell to the membrane edge of the cell; and then
    d) comparing any translocation detected in step (c) to that which occurs in the absence of said test condition;
wherein increased translocation of the detectable molecule in the cell compared to that which occurs in the absence of said test condition indicates increased GPCR activation compared to activation that occurs in the absence of said test condition, and decreased translocation of the detectable molecule in the cell compared to that which occurs in the absence of said test condition indicates decreased GPCR compared to activation that occurs in the absence of said test condition.

2. A method according to claim 1, wherein the test condition is the presence in the cell of a kinase.

3. A method according to claim 1, wherein the test condition is the presence in the cell of a G-protein.

4. A method according to claim 1, wherein the test condition is the exposure of the cell to a compound selected from GPCR agonists and GPCR antagonists.

5. A method according to claim 1 wherein the test condition is co-expression in the cell of a second receptor.

6. A method for screening a β-arrestin protein or fragment thereof for the ability to bind to phosphorylated GPCRs, comprising:
    a) providing a cell that:
        i) expresses at least one GPCR; and
        ii) contains a conjugate comprising a test β-arrestin protein and an optically detectable molecule;
    b) exposing the cell to an agonist for said at least one GPCR; and then
    c) detecting translocation of the detectable molecule from the cytosol of the cell to the membrane edge of the cell;
wherein translocation of the detectable molecule in the cell indicates β-arrestin protein binding to the phosphorylated GPCR.

7. A method for screening a test compound for G protein coupled receptor (GPCR) agonist activity, comprising:
    a) providing a cell expressing a GPCR and containing a conjugate comprising a β-arrestin protein and an optically detectable molecule;
    b) exposing the cell to a test compound; and then
    c) detecting translocation of the detectable molecule from the cytosol of the cell to the membrane edge of the cell;
wherein movement of the detectable molecule from the cytosol to the membrane edge of the cell after exposure of the cell to the test compound indicates GPCR agonist activity of the test compound.

8. A method according to claim 7 wherein the cell expresses a GPCR whose function is known.

9. A method according to claim 7 wherein the cell expresses a GPCR whose function is unknown.

10. A method according to claim 7 wherein the cell expresses an odorant GPCR.

11. A method according to claim 7 wherein the cell expresses a β-adrenergic GPCR.

12. A method according to claim 7 wherein the detectable molecule is Green Fluorescent Protein.

13. A method according to claim 7 wherein the cell is a mammalian cell.

14. A method according to claim 7, wherein the cell is selected from the group consisting of bacterial cells, yeast cells, fungal cells, plant cells and animal cells.

15. A method according to claim 7, wherein the cell endogenously expresses a GPCR.

16. A method according to claim 7, wherein the cell has been transformed to express a GPCR not endogenously expressed by such a cell.

17. A method according to claim 7, where the test compound is in aqueous solution.

18. A method according to claim 7, where the cells are deposited on a substrate prior to said detecting step.

19. A method of screening a sample solution for the presence of an agonist to a G protein coupled receptor (GPCR), comprising:
   a) providing a cell expressing a GPCR and containing a conjugate, the conjugate comprising a β-arrestin protein and an optically detectable molecule;
   b) exposing the cell to a sample solution; and then
   c) detecting translocation of the detectable molecule from the cytosol of the cell to the membrane edge of the cell;
wherein movement of the detectable molecule from the cytosol to the membrane edge of the cell after exposure of the cell to the sample solution indicates the sample solution contains an agonist for a GPCR expressed in the cell.

20. A method according to claim 19, wherein the cell expresses a GPCR whose function is known.

21. A method according to claim 19, wherein the cell expresses a GPCR whose function is unknown.

22. A method according to claim 19 wherein the cell expresses an odorant GPCR.

23. A method according to claim 19 wherein the cell expresses a β-adrenergic GPCR.

24. A method according to claim 19 wherein the detectable molecule is Green Fluorescent Protein.

25. A method according to claim 19 wherein the cell is a mammalian cell.

26. A method according to claim 19, wherein the cell is selected from the group consisting of bacterial cells, yeast cells, fungal cells, plant cells and animal cells.

27. A method of screening a test compound for G protein coupled receptor (GPCR) antagonist activity, comprising:
   a) providing a cell expressing a GPCR, and containing a conjugate, the conjugate comprising a β-arrestin protein and an optically detectable molecule;
   b) exposing the cell to a test compound;
   c) exposing the cell to an agonist for said GPCR; and
   d) detecting translocation of the detectable molecule from the cytosol to the membrane edge of the cell;
where exposure to the agonist occurs at the same time as, or subsequent to, exposure to the test compound, and wherein movement of the detectable molecule from the cytosol to the membrane edge of the cell after exposure of the cell to the test compound indicates that the test compound is not an antagonist for said GPCR.

28. A method according to claim 27 wherein the cell expresses a GPCR whose function is unknown.

29. A method according to claim 27 wherein the cell expresses an odorant GPCR.

30. A method according to claim 27 wherein the cell expresses a β-adrenergic GPCR.

31. A method according to claim 27 wherein the detectable molecule is Green Fluorescent Protein.

32. A method according to claim 27 wherein the cell is a mammalian cell.

33. A method according to claim 27, wherein the cell is selected from the group consisting of bacterial cells, yeast cells, fungal cells, plant cells and animal cells.

34. A method according to claim 27, where the cells are deposited on a substrate prior to said detecting step.

35. A method for screening a test compound for G protein coupled receptor (GPCR) antagonist activity; comprising:
   a) providing a cell expressing a GPCR and containing a conjugate, the conjugate comprising a β-arrestin protein and an optically detectable molecule;
   b) exposing the cell to a GPCR agonist so that translocation of the detectable molecule from the cytosol of the cell to the membrane edge of the cell occurs;
   c) exposing the cell to a test compound; and
   d) detecting translocation of the detectable molecule from the membrane edge of the cell to the cytosol of the cell;
where exposure to the agonist occurs prior to exposure to the test compound, and wherein movement of the detectable molecule from the membrane edge of the cell to the cytosol after exposure of the cell to the test compound indicates that the test compound has a GPCR antagonist activity.

36. A method according to claim 35 wherein the detectable molecule is Green Fluorescent Protein.

37. A method according to claim 35 wherein the cell is a mammalian cell.

38. A method according to claim 35, wherein the cell is selected from the group consisting of bacterial cells, yeast cells, fungal cells, plant cells and animal cells.

39. A method according to claim 35, where the test compound is in aqueous solution.

40. A method according to claim 35, where the cells are deposited on a substrate prior to said detecting step.

41. A method of screening a cell for the presence of a G protein coupled receptor (GPCR) responsive to a GPCR agonist, comprising:
   a) providing a cell, said cell containing a conjugate comprising a β-arrestin protein and an optically detectable molecule;
   b) exposing the cell to a GPCR agonist; and
   c) detecting translocation of the detectable molecule from the cytosol to the membrane edge of the cell;
wherein movement of the detectable molecule from the cytosol to the membrane edge of the cell after exposure of the cell to the GPCR agonist indicates that the cell contain a GPCR responsive to said agonist.

42. A method according to claim 41 wherein the detectable molecule is Green Fluorescent Protein.

43. A method of screening a plurality of cells for those cells which contain a G protein coupled receptor (GPCR) responsive to a GPCR agonist, comprising:
   a) providing a plurality of cells, said cells containing a conjugate comprising a β-arrestin protein and an optically detectable molecule;
   b) exposing the cells to a GPCR agonist; and
   c) detecting those cells in which the detectable molecule is translocated from the cytosol of the cell to the membrane edge of the cell;
wherein movement of the detectable molecule from the cytosol to the membrane edge of a cell after exposure to the GPCR agonist indicates that the cell contains a GPCR for said GPCR agonist.

44. A method according to claim 43 wherein the detectable molecule is Green Fluorescent Protein.

45. A method according to claim 43 wherein the plurality of cells are contained in a tissue.

46. A method according to claim 43 wherein the plurality of cells are contained in an organ.

47. A method according to claim 43 wherein step (b) comprises exposing the cells to a plurality of GPCR agonists.

48. A substrate having deposited thereon a plurality of cells, said cells expressing at least one GPCR and containing a conjugate, the conjugate comprising a β-arrestin protein and a detectable molecule selected from the group consisting of optically detectable molecules and immunologically detectable molecules.

49. A substrate according to claim 48, wherein the detectable molecule is Green Fluorescent Protein.

50. A substrate according to claim 48 wherein the cells are mammalian cells.

51. A substrate according to claim 48, wherein said plurality cells are selected from the group consisting of bacterial cells, yeast cells, fungal cells, plant cells and animal cells.

52. A substrate according to claim 48 wherein the cells express an odorant GPCR.

53. A substrate according to claim 48 wherein the cells express a β-adrenergic GPCR.

54. A substrate according to claim 48, wherein the substrate is made of a material selected from glass, plastic, ceramic, semiconductor, silica, fiber optic, diamond, biocompatible monomer, and biocompatible polymer materials.

55. A method of detecting G protein coupled receptor (GPCR) pathway activity in a cell expressing at least one GPCR and containing β-arrestin protein conjugated to an optically detectable molecule, said method comprising detecting translocation of the detectable molecule from the cytosol of the cell to the membrane edge of the cell, wherein said translocation of the detectable molecule indicates activation of the GPCR pathway.

56. A method according to claim 55 wherein said detectable molecule is Green Fluorescent Protein.

57. A method according to claim 55 wherein said cell is a mammalian cell.

58. A method according to claim 55, wherein the cell is selected from the group consisting of bacterial cells, yeast cells, fungal cells, plant cells and animal cells.

59. A method according to claim 55 wherein the cell expresses a GPCR whose function is known.

60. A method according to claim 55 wherein the cell expresses a GPCR whose function is unknown.

61. A method according to claim 55 wherein the cell expresses an odorant GPCR.

62. A method according to claim 55, wherein the cell expresses a β-adrenergic GPCR.

63. A method according to claim 55, wherein the cell endogenously expresses a GPCR.

64. A method according to claim 55, wherein the cell has been transformed to express a GPCR not endogenously expressed by such a cell.

65. A method according to claim 55, where the cells are deposited on a substrate prior to detecting translocation of the detectable molecule from the cytosol to the membrane edge.

66. A method according to claim 55 wherein said cell is contained in a tissue.

67. A method according to claim 55 wherein said cell is contained in an organ.

68. A method according to claim 1 wherein the cell expresses a taste GPCR.

69. A method according to claim 7 wherein the cell expresses a taste GPCR.

70. A method according to claim 17 wherein the cell expresses a taste GPCR.

71. A method according to claim 27 wherein the cell expresses a taste GPCR.

72. A method according to claim 35 wherein the cell expresses a taste GPCR.

73. A method according to claim 41 wherein the cell expresses a taste GPCR.

74. A method according to claim 55 wherein the cell expresses a taste GPCR.

75. A method according to claim 1 wherein the cell is an insect cell.

76. A method according to claim 7 wherein the cell is an insect cell.

77. A method according to claim 14 wherein the cell is an insect cell.

78. A method according to claim 27 wherein the cell is an insect cell.

79. A method according to claim 35 wherein the cell is an insect cell.

80. A method according to claim 41 wherein the cell is an insect cell.

81. A method according to claim 55 wherein the cell is an insect cell.

82. A method according to claim 43 wherein said plurality of cells are insect cells.

83. A substrate according to claim 48 wherein said plurality of cells are insect cells.

84. A substrate according to claim 48 wherein the cells express a taste GPCR.

* * * * *